United States Patent [19]  [11]  4,160,091
Herron  [45]  Jul. 3, 1979

[54] PROCESS FOR PREPARATION OF 3-HALO-3-METHYLCEPHAMS

[75] Inventor: David K. Herron, Indianapolis, Ind.

[73] Assignee: Eli Lilly and Company, Indianapolis, Ind.

[21] Appl. No.: 853,065

[22] Filed: Nov. 21, 1977

[51] Int. Cl.² ............................................ C07D 501/02
[52] U.S. Cl. .................................. 544/16; 260/239.1; 260/239 A
[58] Field of Search .................. 544/16; 260/239.1

[56] References Cited

PUBLICATIONS

Kamiya et al., Tetrahedron Letters, No. 32, 3001 (1973).
Kukolja et al., J.A.C.S., 97, 3192 (1975).

*Primary Examiner*—Nicholas S. Rizzo
*Attorney, Agent, or Firm*—Steven R. Lammert; Arthur R. Whale

[57] ABSTRACT

3-Halo-3-methylcephams and 2-halomethylpenams are prepared by the reaction of novel azetidinone mercuric sulfides with positive halogenating agents. 3-Halo-3-methylcephams are useful as intermediates to known desacetoxy cephalosporin antibiotics.

10 Claims, No Drawings

PROCESS FOR PREPARATION OF 3-HALO-3-METHYLCEPHAMS

BACKGROUND

Since the discovery of cephalosporins and the expanded antibiotic activity associated therewith a considerable research effort has been directed to methods of synthesis of these bicyclic β-lactam containing compounds. Many researchers have sought to prepare cephalosporins from readily available penicillins. A significant break through in this line of research was preparation of desacetoxycephalosporins directly from penicillins by an acid catalyzed thermal rearrangement of penicillin sulfoxides. This process was first described in U.S. Pat. No. 3,275,626 issued Sept. 27, 1966. Since that time there has issued a multiplicity of patents describing improved methods for the conversion of penicillin sulfoxides to desacetoxycephalosporins (derivatives of 7-ADCA). More recent discoveries of S. Kukolja et al. [Journal of the American Chemical Society, 98, 5040 (1976)] and Dr. G. A. Koppel [U.S. Pat. No. 4,029,651 issued June 14, 1977] has made derivatives of 7-ACA available from penicillin starting materials.

3-Halo-3-methylcephams are known compounds and have been used to prepare desacetoxycephalosporin derivatives. 3-Halo-3-methylcephams like desacetoxycephalosporins have been prepard directly from penicillin sulfoxides. Penicillin sulfoxides react, for example, with thionyl chloride at elevated temperatures [See S. Kukolja et al. Journal of the American Chemical Society, 94, 7169 (1972) and 97, 3192 (1975)] to provide 3-chloro-3-methylcepham compounds. Such compounds have also been prepared by chlorination of the corresponding 3-hydroxy-3-methylcephams.

The present invention is directed to a new process for preparation of 3-halo-3-methylcepham compounds. More specifically the present invention embodies a process for preparing 3-halo-3-methylcapham compounds from penicillin derived monocyclic azetidinone mercuric sulfides via their reaction with positive halogenating agents.

SUMMARY OF THE INVENTION

The present invention is directed to a process for preparing 3-halo-3-methylcepham compounds and 2-halomethylpenam compounds by reacting novel azetidinone mercuric sulfides of the formula

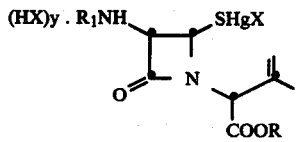

with positive halogenating agents. Both the cepham and penam products from the present process can be converted to desacetoxycephalosporins.

DETAILED DESCRIPTION OF THE INVENTION

This invention provides a process for preparing compounds of the formula

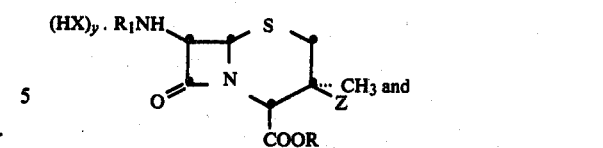

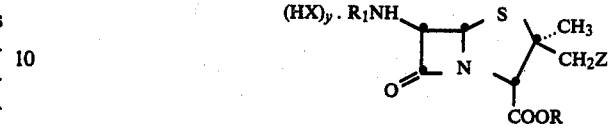

which comprises reacting a compound of the formula

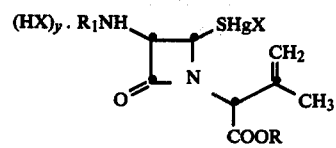

with at least an equivalent amount of a positive halogenating agent selected from the group consisting of chlorine, sulfuryl chloride, tert-butylhypochlorite, bromine and sulfuryl bromide in an inert organic solvent wherein in the above formula, X is chloro or bromo, R is hydrogen or a carboxylic acid ester protecting group, $R_1$ is hydrogen or an acyl group derived from a carboxylic acid, Z is chloro or bromo and y is 0 or 1 provided that when $R_1$ is an acyl group y is 0.

In the foregoing description of the present invention the term carboxylic acid ester protecting group has reference to the commonly used ester groups employed to block or protect the carboxylic acid functionality while reactions involving other functional sites are carried out. Such carboxy protecting groups are noted for their ease of cleavage by hydrolytic or hydrogenolytic methods to the corresponding carboxylic acid. Examples of carboxylic acid ester protecting groups are methyl, tert-butyl, 1-methylcyclohexyl, benzyl, 4-methoxybenzyl, 4-nitrobenzyl, $C_2$–$C_6$ alkanoyloxymethyl, 2-iodoethyl, 2-bromoethyl, diphenylmethyl (benzhydryl), phenacyl, 4-halophenacyl, dimethylallyl, 2,2,2-trichloroethyl, $C_1$–$C_3$ alkoxymethyl, tri($C_1$–$C_3$ alkyl)silyl, and succinimidomethyl. Other known carboxylic acid protecting groups are described by E. Haslam in "Protective Groups in Organic Chemistry," J. F. W. McOMie, Ed., Plenum Press, New York, New York, 1973, Chapter 5. The nature of such groups is not critical; however, because of availability and ease of handling, certain carboxylic acid ester protecting groups are preferred. For the present process preferred carboxylic acid protecting groups are tert-butyl, 4-methoxybenzyl, 4-nitrobenzyl, benzhydryl and 2,2,2-trichloroethyl.

Likewise the nature of $R_1$ is not critical in the present process. $R_1$ can be hydrogen, representing the free amine or the amine acid addition salts, or $R_1$ can be an acyl group derived from a carboxylic acid. Exemplary of such acyl groups are those groups of the formula

wherein $R_2$ is (a) C₁-C₄ alkyl or halo-C₁-C₄ alkyl;

(b) benzyloxy, 4-nitrobenzyloxy, 4-methoxy benzyloxy, tert-butoxy, 2,2,2-trichloroethoxy, or benzhydryloxy;

(c) the group R₃ wherein R₃ is 1,4-cyclohexadienyl, phenyl, or phenyl substituted with 1 or 2 substituents selected from the group consisting of chloro, bromo, iodo, hydroxy, nitro, cyano, trifluoromethyl, C₁-C₄ alkyl or C₁-C₄ alkoxy;

(d) arylalkyl group of the formula

wherein R₃ is as defined above and m is 1 or 0;

(e) a substituted arylalkyl group of the formula

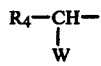

wherein R₄ is R₃ as defined above, 2-thienyl, or thienyl and W is hydroxy, formyloxy, chloroacetoxy, benzyloxy, 4-methoxybenzyloxy, carboxy, tert-butoxycarbonyl, benzyloxycarbonyl, 4-methoxybenzyloxycarbonyl, 4-nitrobenzyloxycarbonyl, benzhydryloxycarbonyl, 2,2,2-trichloroethoxycarbonyl, amino, ammonium, tert-butoxycarbonylamino, benzyloxycarbonyl, 4-nitrobenzyloxycarbonylamino, 4-methoxybenzyloxycarbonylamino, benzhydryloxycarbonylamino, and 2,2,2-trichloroethoxycarbonylamino; or (f) a heteroarylmethyl group of the formula

wherein R₅ is 2-thienyl, 3-thienyl, 2-furyl, 2-thiazolyl, 5-tetrazolyl, 1-tetrazolyl or 4-isoxazolyl.

The term "C₁-C₄ alkyl" refers to methyl, ethyl, isopropyl, n-propyl, isobutyl, n-butyl and like groups. Exemplary of "C₁-C₄ alkoxy" are methoxy, ethoxy, isopropoxy, tert-butoxy, n-propoxy and like groups. "Halo-C₁-C₄ alkyl" refers to chloromethyl, bromomethyl, iodoethyl, 2-chloropropyl, 3-bromopropyl, 2-iodobutyl, 3-chlorobutyl, 1-chlorobutyl and like groups.

As stated hereinabove the nature of the group R₁ in the foregoing formulas is not critical. The flexibility of the present process with respect to the nature of R₁ is exemplified by the fact that the starting material can be the free amine or amine acid addition salt (R₁ = hydrogen). Because the starting materials for the present process wherein R₁ is hydrogen are readily available, and because the product mixture from the present process wherein R₁ is hydrogen can be conveniently acylated as desired using standard acylation techniques, it is preferred that R₁ be hydrogen in the present process. It should be noted, however, that the starting material wherein R₁ is hydrogen can first be acylated, as described hereinbelow, and subsequently subjected to the conditions of the present process to provide the indicated penam and cepham products wherein R₁ is an acyl group derived from a carboxylic acid.

The starting materials for the process of the present invention are derived from known thiazolineazetidinones of the formula

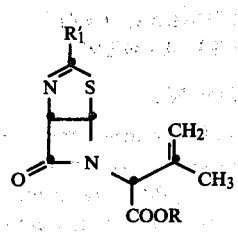

wherein R₁' is, for example, benzyl or phenoxymethyl, by their reaction with mercuric halides in an inert organic solvent in the presence of a primary or secondary C₁-C₈ alcohol or C₁-C₈ diol. Thus, preferred starting materials of the formula

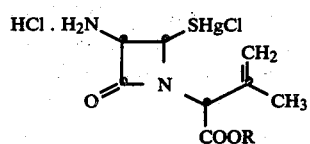

can be prepared by the room temperature reaction of a known thiazolineazetidinone of the structure depicted above with 1.1 equivalents of mercuric chloride in methylene chloride in the presence of about 5 equivalents of propylene glycol. When mercuric bromide is used in place of mercuric chloride the product is a compound in which each chlorine atom in the above formula is replaced by bromine.

Acylation of the foregoing 3-amino azetidinone starting materials using conventional acylation techniques provides the acylated starting materials for the present process. The acylation can be carried out with an active derivative of the carboxylic acid R₃COOH wherein R₃ is as defined above. Of course, any functional groups on the carboxylic acid moiety which could interfere with the acylation reaction such as free hydroxy, amino or carboxy groups should first be protected or blocked with one of the conventional protecting groups. Active derivatives of these acids include acyl halides such as acid chlorides or bromides, the acid azides, and the mixed anhydrides formed with methyl chloroformate, ethyl chloroformate or isobutyl chloroformate. The acylation can be carried out with the free carboxylic acid with a condensing agent such as dicyclohexylcarbodiimide as described in U.S. Pat. No. 3,218,318. Also the acylation can be effected using the ester formed by the reaction of the carboxylic acid (R₃COOH) and 1-hydroxybenzotriazole in the presence of dicyclohexylcarbodiimide as a condensing agent.

Typically the present process is carried out simply by adding excess halogenating agent to a suspension or solution of the azetidinone mercuric sulfide starting material in an inert organic solvent at room temperature.

The temperature at which the present process is carried out is not critical. Higher or lower temperatures can be employed but without advantage over the preferred room temperature (about 20° to about 30° C.) reactions.

Any of a wide variety of inert organic solvents may be employed as a medium for the present process. By "inert organic solvent" is meant an organic solvent which, under the conditions of the process does not enter into any appreciable reaction with either the reactants or the products. Suitable solvents include for example, aromatic hydrocarbons, such as benzene, toluene, xylene, chlorobenzene, nitrobenzene, and the like; halogenated aliphatic hydrocarbons, such as chloroform, methylene chloride, carbon tetrachloride, 1,2-dichloroethane (ethylene chloride), 1,1,2-trichloroethane, and 1,1-dibromo-2-chloroethane; esters such as ethyl acetate and methyl acetate; ethers such as dioxane, tetrahydrofuran, diethyl ether, disopropyl ether and 1,2-dimethoxyethane; nitriles such as acetonitrile or propionitrile; and other solvents including, among others, nitromethane, dimethylformamide, dimethylacetamide, acetone and methyl ethylketone. Preferred solvents are the halogenated aliphatic hydrocarbons. Most preferred is methylene chloride.

Suitable positive halogenating agents are chlorine, sulfuryl chloride, tert-butyl hypochlorite, bromine, and sulfuryl bromide. Chlorinating agents are preferred. Chlorine is most preferred.

At least an equivalent amount of positive halogenating agent is employed. It is preferred however, that an excess of halogenating agent be employed in the present process. Typically a 2 to 10 fold excess of halogenating is used.

As described hereinabove both 2-halomethylpenams and 3-halo-3-methylcephams are produced in the present process. The use of a chlorinating agent in the present process provides the chloromethyl penams and the chlorocephams while the use of brominating agents provides a mixture of the corresponding bromo derivatives. The product mixture can be reacted, without separation, with an organic base such as pyridine or thiethylamine in methylene chloride to provide a product mixture containing the corresponding desacetoxycephalosporin of the formula

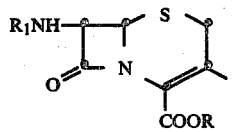

wherein $R_1$ is an acyl group derived from a carboxylic acid and R is hydrogen or a carboxylic acid protecting group. The desacetoxycephalosporin can be isolated by column chromatography.

Alternatively, the products produced in accordance with the present process can be separated and purified by employing conventional laboratory techniques. These include filtration, crystallization, recrystallization, trituration, and chromatography. Where the product is a mixture of a 6-amino penam and a 7-amino cepham compound the mixture is usually acylated using one of the aforedescribed conventional acylating techniques, before the mixture is separated, typically by chromatographic means, into the component products.

The 6-acylamino-2-halomethyl-2-methylpenams derived by the present process can be converted to desacetoxycephalosporins by reaction with silver salts. [See S. Kukolja et al. *Journal of the American Chemical Society*, 97, 3192(1975)].

Dehydrohalogenation of the 3-halo-3-methylcepham products of the present process is accomplished by treatment with an organic base such as pyridine or triethylamine in methylene chloride to provide the corresponding desacetoxycephalosporins.

Cleavage of the carboxylic acid protecting group on the desacetoxycephalosporin products can be achieved by well-known methods. Thus, where the carboxylic acid protecting group is benzhydryl, tert-butyl, 4-methoxybenzyl, or 1-methylcyclohexyl, deesterification is accomplished by treatment of the ester with an acid such as trifluoroacetic acid, in the presence of anisole. The 2-iodoethyl, 2-bromoethyl, 4-nitrobenzyl and 2,2,2-trichloroethyl protecting groups are removed with zinc and an acid such as acetic or hydrochloric acid. The 4-nitrobenzyl protecting group can also be removed by hydrogenation in the presence of palladium, platinum, rhodium or a compound thereof, in suspension or on a carrier such as barium sulfate, carbon, alumina or the like. Other carboxy protecting groups are removed by hydrolysis under basic conditions.

The antibiotic activity of the resulting cephem acids has been well documented. One such cephem acid is cephalexin ($R_1$ in the above formula =

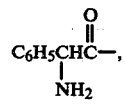

R=H), a compound of substantial clinical and commercial significance. The following examples are provided to further illustrate this invention.

EXAMPLE 1

4'-Nitrobenzyl 7-phenoxyacetamido-3β-chloro-3α-methylcepham4-carboxylate.

To a suspension of 1.22 g (2 mmol) of [[1-[1-(4-nitrobenzyloxycarbonyl)-2-methylprop-2-enyl]-3-amino4-oxo-2-azetidinyl]thio]mercury chloride hydrochloride in 200 ml of methylene chloride at room temperature was added 2.6 ml of a 1.6 M solution of chlorine in methylene chloride. The mixture immediately became homogeneous and thereafter a precipitate formed. After 30 minutes the reaction mixture was evaporated in vacuo to dryness. Trituration of the resulting product provided 300 mg of a product identified as a mixture of the hydrochloride salts of 4'-nitrobenzyl 6-amino-2α-methyl-2β-chloromethylpenam-3-carboxylate and 4'-nitrobenzyl 7-amino-3β-chloro-3α-methylcepham-4-carboxylate. The product mixture was then acylated, without purification or separation, by dissolving the mixture in a solution of 16 ml of acetonitrile and 4 ml of propylene oxide, and adding 0.25 ml (2 mmol) phenoxyacetyl chloride. After 2 hours the reaction mixture was evaporated in vacuo to dryness. The residue was dissolved in ethyl acetate and washed successively with dilute hydrochloric acid, aqueous sodium bicarbonate and brine, and then dried over anhydrous sodium sulfate. Evaporation in vacuo to dryness provided a mixture of 2 major products as determined by thin layer chromatography (silica gel, 1:1/ethyl acetate-hexane). Separation by preparative thin layer chromatography gave 151 mg (29% yield) of 4'-nitrobenzyl 6-phenoxyacetamido2β-chloromethyl-2α-methylpenam-3-carboxylate [nmr(CDCl$_3$) δ 1.51 (s, 3, 2α-CH$_3$), 3.5 (s, 2, 2β-CH$_2$Cl), 4.57 (s, 2, side chain CH$_2$), 5.05 (s, 1, C-3 H), 5.33 (s, 2, ester CH$_2$), 5.67 (m, 2, azetidinone protons), and 6.8-8.3 (m, 9, ArH)] and 56 mg (11%) of 4'-nitrobenzyl 7-phenoxyacetamido 3β-chloro-3α-methylcepham-4-carboxylate [nmr(CDCl$_3$) δ 1.67 (s, 3, CH$_3$), 2.75 and 3.67 (ABq, 2, J=14 Hz, C$_2$-H), 4.83 (s, 1, C-4 H), 5.40 (d, 1, J=4.5 Hz, C-6 H) and 5.75 (q, 1, J=4.5 and 8.0 Hz, C-7 H).

EXAMPLE 2

The same procedure was followed as described in Example 1 with the exception that 20 ml of the 1.6 M. chlorine solution was used. The large excess of chlorine employed here had no apparent effect on the course of the reaction. An nmr of the crude product mixture was identical to an nmr of the intermediate product mixture obtained in Example 1.

EXAMPLE 3

The same procedure was followed as in Example 1 except that the reaction was carried out in dimethylformamide. Comparative thin layer chromatography showed the product mixture, after acylation with phenoxyacetyl chloride, to have the same major components as the product mixture from Example 1.

I claim:

1. A process for preparing compounds of the formula

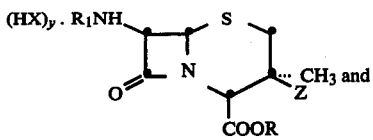 and

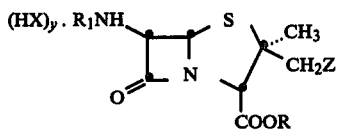

which comprises reacting a compound of the formula

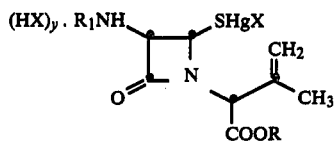

with at least at equivalent of a positive halogenating agent selected from the group consisting of chlorine, sulfuryl chloride, tert-butylhypochlorite, bromine and sulfuryl bromide in an inert organic solvent wherein in the above formula, X is chloro or bromo, R is hydrogen or a carboxylic acid ester protecting group, $R_1$ is hydrogen or an acyl group derived from a carboxylic acid, Z is chloro or bromo and y is 0 or 1 provided that when $R_1$ is an acyl group y is 0.

2. The process of claim 1 wherein $R_1$ is an acyl group derived from a carboxylic acid.
3. The process of claim 1 wherein $R_1$ is hydrogen.
4. The process of claim 3 wherein X is chloro.
5. The process of claim 4 wherein R is a carboxylic acid ester protecting group.
6. The process of claim 4 wherein the inert organic solvent is a halogenated aliphatic hydrocarbon.
7. The process of claim 6 wherein Z is bromo and the positive halogenating agent is bromine or sulfuryl bromide.
8. The process of claim 6 wherein Z is chloro and the positive halogenating agent is chlorine, sulfuryl chloride, or tert-butyl hypochloride.
9. The process of claim 8 wherein the inert organic solvent is methylene choride.
10. The process of claim 9 wherein [[1-[1-(4-nitrobenzyloxycarbonyl)-2-methylprop-2-enyl]-3-amino-4-oxo-2-azetidinyl]thio]mercury chloride hydrochloride is reacted with about a 4-fold excess of chlorine.

* * * * *